United States Patent
Wang et al.

(10) Patent No.: US 6,447,835 B1
(45) Date of Patent: Sep. 10, 2002

(54) METHOD OF COATING POLYMERIC TUBES USED IN MEDICAL DEVICES

(75) Inventors: Lixiao Wang; Yiqun Wang, both of Maple Grove; Dachuan Yang, Plymouth, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/504,194

(22) Filed: Feb. 15, 2000

(51) Int. Cl.[7] .................. A61L 27/00; B05D 7/22; B05D 5/08
(52) U.S. Cl. .................. 427/2.24; 427/2.1; 427/2.25; 427/2.28; 427/2.3; 427/230; 427/236; 427/422; 264/211; 264/209.1; 264/177.14
(58) Field of Search .................. 427/2.1, 2.24, 427/2.25, 2.28, 2.3, 230, 236, 422; 264/177.14, 209.1, 211

(56) References Cited

U.S. PATENT DOCUMENTS

| | | | |
|---|---|---|---|
| 4,056,344 A | * 11/1977 | Lemelson | 425/132 |
| 4,080,476 A | * 3/1978 | Laskey | 428/413 |
| 4,299,256 A | 11/1981 | Bacehowski et al. | 138/137 |
| 4,373,009 A | 2/1983 | Winn | 428/424.2 |
| 4,490,421 A | 12/1984 | Levy | 428/35 |
| 4,720,521 A | 1/1988 | Spielvogel et al. | 524/862 |
| 4,939,007 A | 7/1990 | Hu et al. | 428/34.1 |
| 5,059,269 A | * 10/1991 | Hu et al. | 156/244.11 |
| 5,061,424 A | 10/1991 | Karimi et al. | 264/171 |
| 5,084,315 A | * 1/1992 | Karimi et al. | 428/36.6 |
| 5,102,401 A | 4/1992 | Lambert et al. | 604/264 |
| 5,125,913 A | 6/1992 | Quackenbush | 604/264 |
| 5,156,785 A | 10/1992 | Zdrahala | 264/108 |
| 5,195,969 A | 3/1993 | Wang et al. | 604/96 |
| 5,248,305 A | 9/1993 | Zdrahala | 604/280 |
| 5,254,090 A | 10/1993 | Lombardi et al. | 604/96 |
| 5,266,359 A | 11/1993 | Spielvogel | 427/388.4 |
| 5,348,536 A | 9/1994 | Young et al. | 604/43 |
| 5,348,538 A | 9/1994 | Wang et al. | 604/96 |
| 5,503,631 A | 4/1996 | Onishi et al. | 604/96 |
| 5,509,899 A | 4/1996 | Fan et al. | 604/96 |

(List continued on next page.)

FOREIGN PATENT DOCUMENTS

| | | |
|---|---|---|
| DE | 27 52 969 A1 | 5/1979 |
| JP | 10277144 | 10/1998 |
| WO | 99/65556 | 12/1999 |
| WO | 00/56248 | 9/2000 |
| WO | 00/67828 | 11/2000 |

Primary Examiner—Shrive P. Beck
Assistant Examiner—Jennifer Kolb Michener
(74) Attorney, Agent, or Firm—Vidas, Arrett & Steinkraus P.A.

(57) ABSTRACT

The present invention relates to a method of preparing a coated hollow polymeric tubular member useful in medical devices. The method involves a simple, unique method of simultaneously extruding and coating the polymeric tube.

23 Claims, 3 Drawing Sheets

U.S. PATENT DOCUMENTS

| | | | |
|---|---|---|---|
| 5,538,510 A | 7/1996 | Fontirroche et al. | 604/265 |
| 5,573,720 A | 11/1996 | Kotzer | 264/171.15 |
| 5,576,072 A | 11/1996 | Hostettler et al. | 427/532 |
| 5,662,960 A | 9/1997 | Hostettler et al. | 427/2.3 |
| 5,695,789 A | 12/1997 | Harris | 425/131.1 |
| 5,714,110 A * | 2/1998 | Wang et al. | 264/529 |
| 5,725,814 A | 3/1998 | Harris | 264/40.3 |
| 5,736,251 A | 4/1998 | Pinchuk | 428/447 |
| 5,741,452 A | 4/1998 | Ryan et al. | 264/209.5 |
| 5,746,745 A | 5/1998 | Abele et al. | 606/108 |
| 5,769,817 A | 6/1998 | Burgmeier | 604/96 |
| 5,820,594 A | 10/1998 | Fontirroche et al. | 604/96 |
| 5,824,173 A * | 10/1998 | Fontirroche et al. | 156/86 |
| 5,849,368 A | 12/1998 | Hostettler et al. | 427/536 |
| 5,863,366 A | 1/1999 | Snow | 156/143 |
| 5,894,042 A * | 4/1999 | Ferralli | 428/36.91 |
| 5,902,287 A | 5/1999 | Martin | 604/280 |
| 5,919,570 A | 7/1999 | Hostettler et al. | 428/424.8 |
| 6,004,289 A | 12/1999 | Saab | 604/96 |
| 6,004,310 A | 12/1999 | Bardsley et al. | 604/524 |
| 6,016,848 A | 1/2000 | Egres, Jr. | 138/137 |
| 6,017,577 A | 1/2000 | Hostettler et al. | 427/2.12 |
| 6,024,722 A | 2/2000 | Rau et al. | 604/96 |
| 6,027,477 A | 2/2000 | Kastenhofer | 604/96 |
| 6,030,369 A | 2/2000 | Engelson et al. | 604/264 |
| 6,030,656 A | 2/2000 | Hostettler et al. | 427/2.3 |
| 6,040,058 A | 3/2000 | Hostettler et al. | 428/457 |
| 6,046,143 A | 4/2000 | Khan et al. | 508/208 |
| 6,071,266 A * | 6/2000 | Kelley | 604/265 |

* cited by examiner

METHOD OF COATING POLYMERIC TUBES USED IN MEDICAL DEVICES

FIELD OF THE INVENTION

The present invention relates to a unique coating process that involves the simultaneous extrusion and coating of polymeric tubes.

BACKGROUND OF THE INVENTION

Medical devices for insertion into the body such as catheters and dilatation balloons attached to the distal end of such catheters, are formed from polymeric materials such as polyolefins including polypropylene and polyethylene, ethylene copolymers, polyvinyl chloride, polyurethane, polyesters, polyamides, polyether block amide elastomers, other thermoplastic elastomers, and so forth. These materials are typically inherently nonlubricious. It is desirable that these surfaces be lubricated for a variety of reasons including the reduction of catheter or wire movement frictions, the minimization of thrombosis, tissue trauma, tissue adhesion, pain, and so forth.

Coatings are commonly used in the medical device area for rendering such inherently non-lubricious substrate surfaces lubricious, as well as for protecting the surfaces of these devices, especially dilatation balloons. These coatings may be either hydrophilic or hydrophobic. Furthermore, because such medical devices are often inserted through the skin and into the body and are withdrawn at a later time, or as noted above, travel over long distances through small orifices, it is also necessary to have coatings which can be retained on the surface of the device for a long period, even when exposed to an aqueous environment, and is stable throughout the medical procedure.

Common hydrophobic coatings include fluoropolymers, siloxanes, mineral oil, sesame oil, glycerine, olive oil, polytetrafluoroethylene, and so forth. Hydrophobic coatings of an oily nature, have low surface energies and have a tendency to bead up and migrate over the surface of the device.

Another approach for reducing the coefficient of friction is to add a layer of a low friction material such as polytetrafluoroethylene, hereinafter PTFE and commonly known by the tradename of Teflon®. The problem with the use of PTFE is that it typically requires a separate extrusion process, and also requires etching. Adhesion is also generally a problem between the PTFE and the polymeric materials from which medical devices are made.

Hydrophilic coatings, upon exposure to an aqueous environment, can also migrate from the surface of the device which decreases the efficacy of the lubricious coating, particularly when the coating is in a liquid or gelled state.

There have been a variety of approaches utilized in order to increase the retention time of coatings on the surface of the medical device. These methods include altering the surface of the device such as through high energy radiation, bonding the coating to the surface of the device by direct chemical bonding, in situ polymerization processes, or by forming interpolymer networks.

The radiation process suffers from inconsistency and unreliability in alteration of the polymeric surface, and can produce radiation damage to the substrate. Interpolymer networks can be disrupted and break with turbulent flow, or with extended periods of exposure to an aqueous environment, resulting in the hydrophilic portion washing away from the surface of the device. Chemical bonding and in situ polymerization often decreases process efficiency due to the fact that typically several steps are involved in such a process.

In U.S. Pat. No. 4,373,009 to Winn, a substrate surface is primed with solution of a polyisocyanate, followed by a solution of a hydrophilic copolymer. The hydrophilic copolymer is capable of chemically reacting with a coupling agent which will promote adhesion to the substrate.

U.S. Pat. No. 4,720,521 to Spielvogel describes a film-forming silicone composition having a non-reactive lubricating component which is a siloxane polymer dispersed or distributed within a reactive component which is a mixture of siloxane polymers, such that when the composition is applied to or used in conjunction with a substrate surface, it coats and adheres to the surface while providing surface lubrication.

U.S. Pat. No. 5,084,315 issued Jan. 28, 1992 to Karimi et al. describes a coating composition which has at least two and preferably three or more components. The first component is a hydrophilic lubricating polymer which provides lubricity to the coated article when wet. The second component is a polymeric matrix material which serves as a carrier for the lubricating polymer and as a binder to provide adherence of the coating composition to the base polymer. The nature of the matrix polymer depends on the base polymer and preferably includes a polyurethane. For instance, when the base polymer is PVC, the matrix material preferably is an alloy of PVC and the matrix polyurethane.

U.S. Pat. No. 5,266,359 issued Nov. 30, 1993 to Spielvogel describes a coating composition for an article which comprises an aqueous emulsion of a surfactant and a non-curing polysiloxane lubricant substituted by a polar group, referred to by Spielvogel as the polar lubricant. Spielvogel states that the lubricant used on a metal article, because of the polar group, is adsorbed into the metal and adheres to the surface significantly reducing the wipe-away that occurs when inserting the medical device into the skin. Spielvogel discloses that a plastic catheter tubing may also be coated with the polar lubricant, but preferably is coated with a nonpolar polysiloxane lubricant, and specifically mentioned is trialkylsiloxy terminated polysiloxane.

U.S. Pat. No. 5,919,570 to Hostettler et al. issued Jul. 6, 1999 describes tenaciously adhering coatings of commingled hydrogels composed of a polyurethane/urea polymer hydrogel in combination with at least one dissimilar hydrogel, i.e. poly(N-vinylpyrrolidone) polymer hydrogel, and a process for making such commingled hydrogels, especially where the substrate materials to which they are applied are polymeric materials which are intrinsically non-polar and hydrophobic. Hostettler et al. further describes a process whereby the surface of the hydrophobic polymers are treated in order to render them more polar and hydrophilic so that the tenaciously adhering, slippery commingled hydrogel coatings may subsequently be applied to the polymer surface.

U.S. Pat. No. 5,824,173 issued Oct. 28, 1998 to Fontirroche et al. describes a method of making an intravascular balloon catheter which includes forming an inner shaft by coextruding a flexible plastic tube by bringing a molten outer plastic layer into contact with a molten inner plastic layer, thereby bonding the plastic layers together during the coextrusion process. The inner plastic layer may be more lubricious than the outer plastic layer.

U.S. Pat. No. 5,061,424 issued Oct. 29, 1991 to Karimi et al. describes a method for coextruding a melt of a substrate polymer and a melt of a coating composition comprising polyvinylpyrrolidone and a base polyurethane which gives a shaped article of a substrate polymer with a layer of a coating composition that becomes lubricious when the substrate comes into contact with a liquid.

Surprisingly, the influence of the chemical and physical composition of body fluids, as well as the dynamic forces of the bodily fluids, has a drastic influence on the permanence or retention of the coatings used on medical devices. Hydrophilic polymers may be washed from the surface by bodily fluids and silicone coatings tend to bead and lose their efficacy in the presence of bodily fluids.

Accordingly, there remains a need in the art of medical devices for coatings that are both lubricious and increase the durability of the balloon which have superior retention or wear permanence on the surface of medical devices, especially those constructed from polymeric materials.

SUMMARY OF THE INVENTION

The present invention relates to a method of applying a lubricious and protective coating to a polymeric tube simultaneously with extrusion of the tube while the tube is at temperatures of greater than ambient. The tube may be coated on the inside and/or outside as it is being extruded. It is an object of the present invention to provide a one step process that combines the extrusion and coating processes of tubular members that may be used in medical devices. A thin coating is preferably provided on the inside of the tubular member. The coating method, in addition to providing efficiency in the manufacturing process, also provides improved adhesion, and retention, of a lubricious coating to a polymeric medical device.

Specifically, the present invention relates to a method of preparing a coated hollow polymeric tube by extrusion. The tube has an inner surface and an outer surface. The method involves forcing a stream of molten base polymer into an entry port at one end of an extruder shaping die, and applying a coating to the base polymer while it is in the shaping die of the extruder, and prior to the tube exiting the discharge port of the shaping die. The coating is therefore applied while the tube is in its molten form. The coating may be applied either to the inner surface of the tube, or to the outer surface of the tube.

This coating method simplifies the process while improving adhesion without surface priming or chemical bonding. Applying the coating to the polymeric tube during extrusion while the tube is above ambient temperature provides better adhesion of the coating to the tube.

These coated tubes may be used in medical devices such as catheter assemblies.

DETAILED DESCRIPTIONS OF THE PREFERRED EMBODIMENTS

The following description of the preferred embodiments of the present invention is merely illustrative in nature. One of skill in the art would understand that numerous modifications may be made to the present invention without departing from the true spirit and scope of the present invention.

Generally, a stream of a viscous melt of the base polymer is forced under pressure in a continuous stream through an entry port (20) from extruder mounted at one end of the shaping die 10. The viscous melt typically exits the extruder die at a discharge port 46 into a cool water bath.

Figure 1:
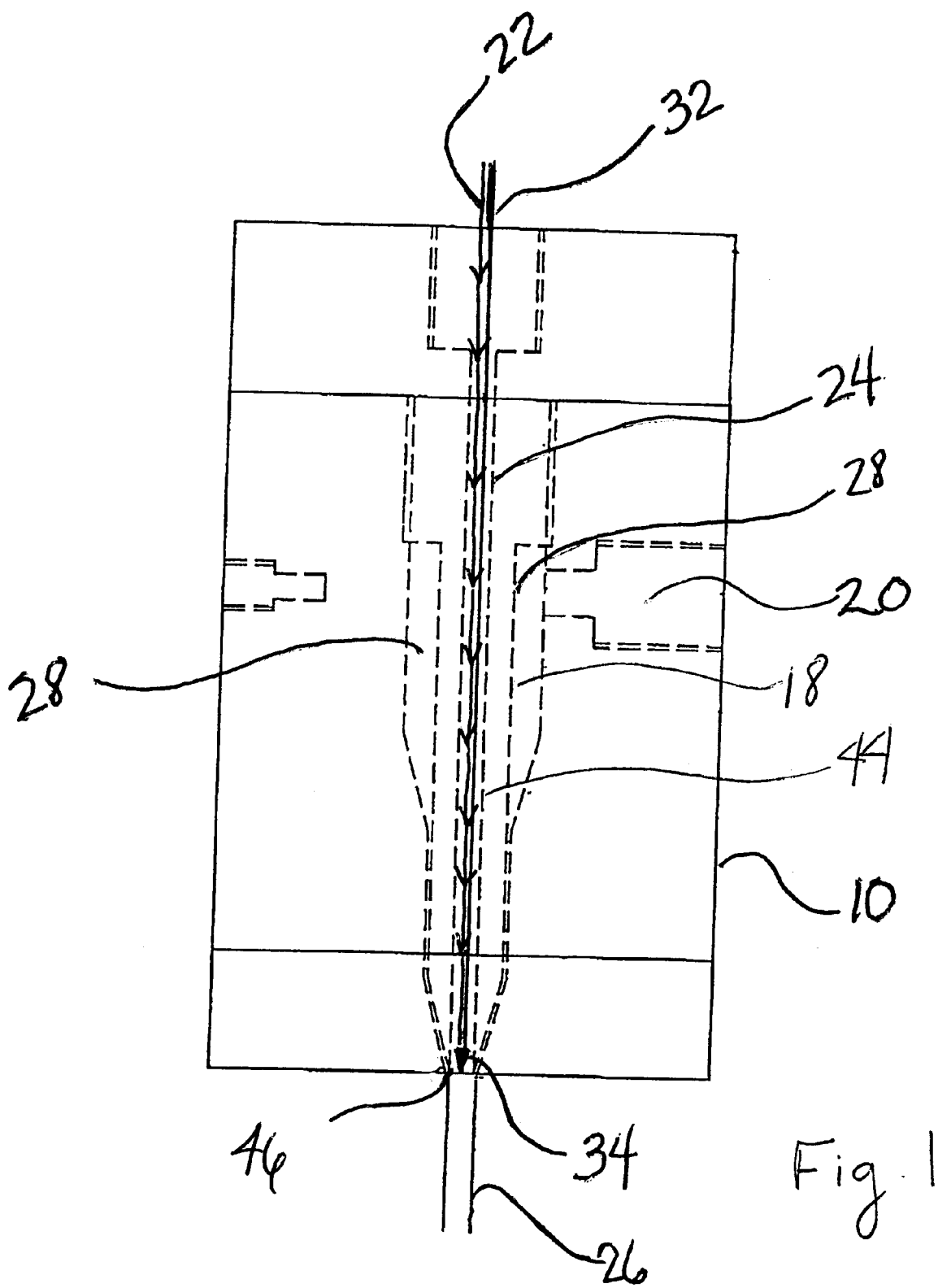
FIG. 1 shows generally at 10, an extrusion crosshead or extrusion shaping head designed for forming tubular members which can be used in medical devices. The tubular member is formed of a thermoplastic polymeric material. The extrusion unit has a nozzle through which the coating may be applied the inside of the polymeric tubular member.

FIG. 1 illustrates generally at 10, an extrusion shaping head or crosshead for forming polymeric tubular members useful in medical devices. Extrusion Head has an entry port 20 from extruder located at a first end of the extruder shaping mandrel 18 which supplies a stream of molten thermoplastic material to flow channel 28. The molten thermoplastic material flows in channel 28 around an air flow channel 44 through which an air source 22 flows for keeping the diameter of the tubing consistent through the use of pressure. The molten polymeric material flows around the extruder shaping mandrel 18 through a discharge port 46 located at one end of the extruder shaping mandrel 18 forming hollow tubing 26 which flows into a cool water bath. A nozzle 34 with a supply means 32 for supplying coating material to the nozzle 34 applies coating to the inner surface of the extruded polymeric tubing 26. The nozzle 34 generally applies the coating by spraying means. The coating is applied to the extruded tubing 26 at the nozzle head 34 prior to exiting of the tubing 26 from the discharge port 46 located at a second end of the extruder shaping mandrel 18 prior to cooling of the tubing 26, and while tubing 26 is at temperatures of approximately 150–300° C.

Figure 2:
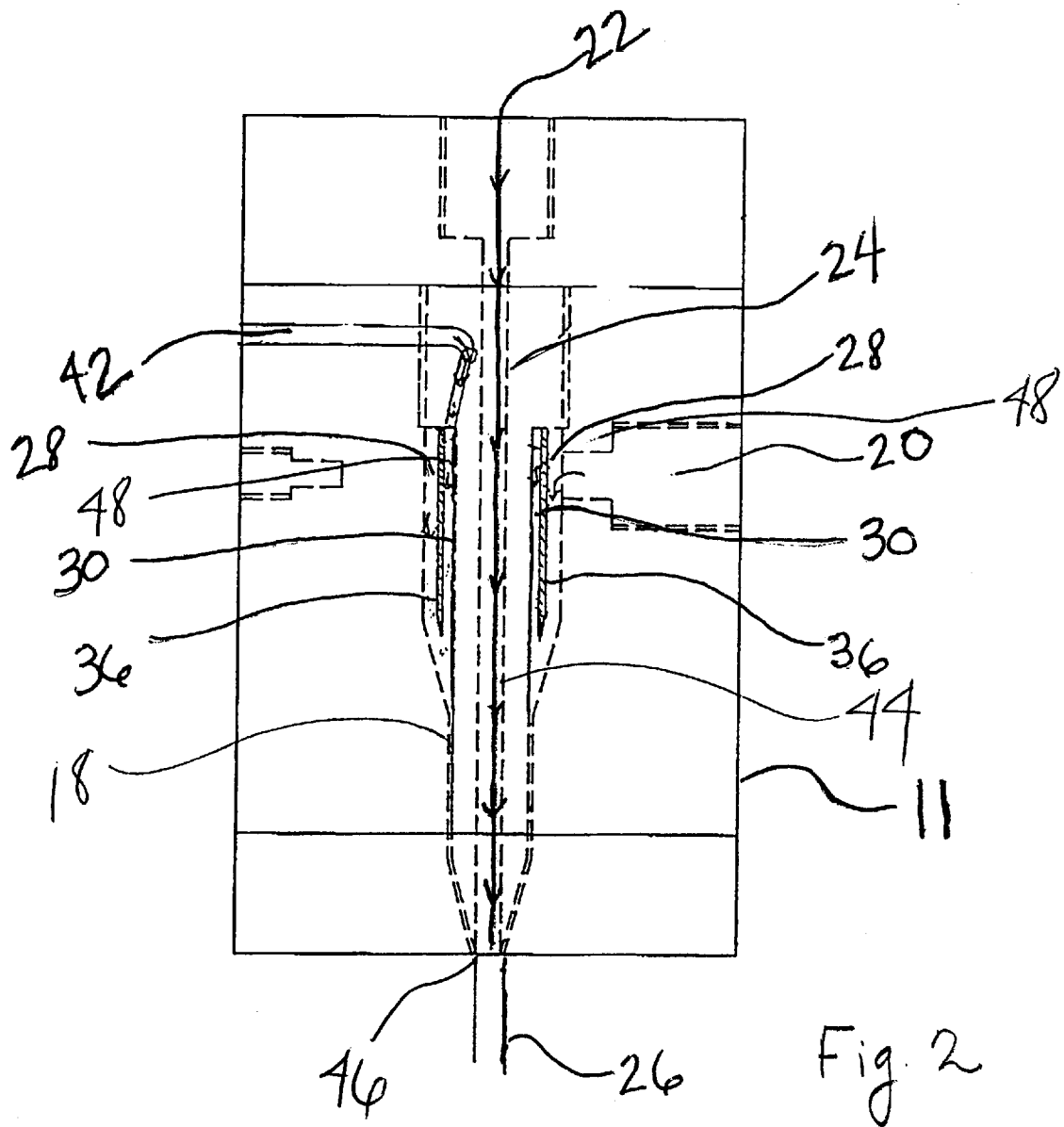
FIG. 2 shows generally at 11, an extrusion crosshead or extrusion shaping head designed for forming hollow tubular members which can be used in medical devices. The extrusion unit has a channel 42 for coextrusion of a coating on the inner surface of the polymeric tube.

FIG. 2 shows generally at 11 an extrusion shaping head or crosshead unit for forming polymeric tubing. The extruder configuration is similar to that found in FIG. 1. The extruder unit has an entry port 20 located at a first end of the shaping mandrel 18 for supplying a stream of molten polymeric material to a channel 28. Additionally, crosshead has a second entry port 42 for supplying a coating to channel 48. The coating composition may be pumped through a second entry port 42 and into the channel 48 using a volumetric gear pump. This allows application of the coating to the inner surface of the hollow tubular member as it is being extruded at high temperatures of about 200° C., thereby improving the adhesion between the tubing and the coating. In other respects, the extruder units in FIG. 1 and FIG. 2 are substantially the same.

Figure 3:
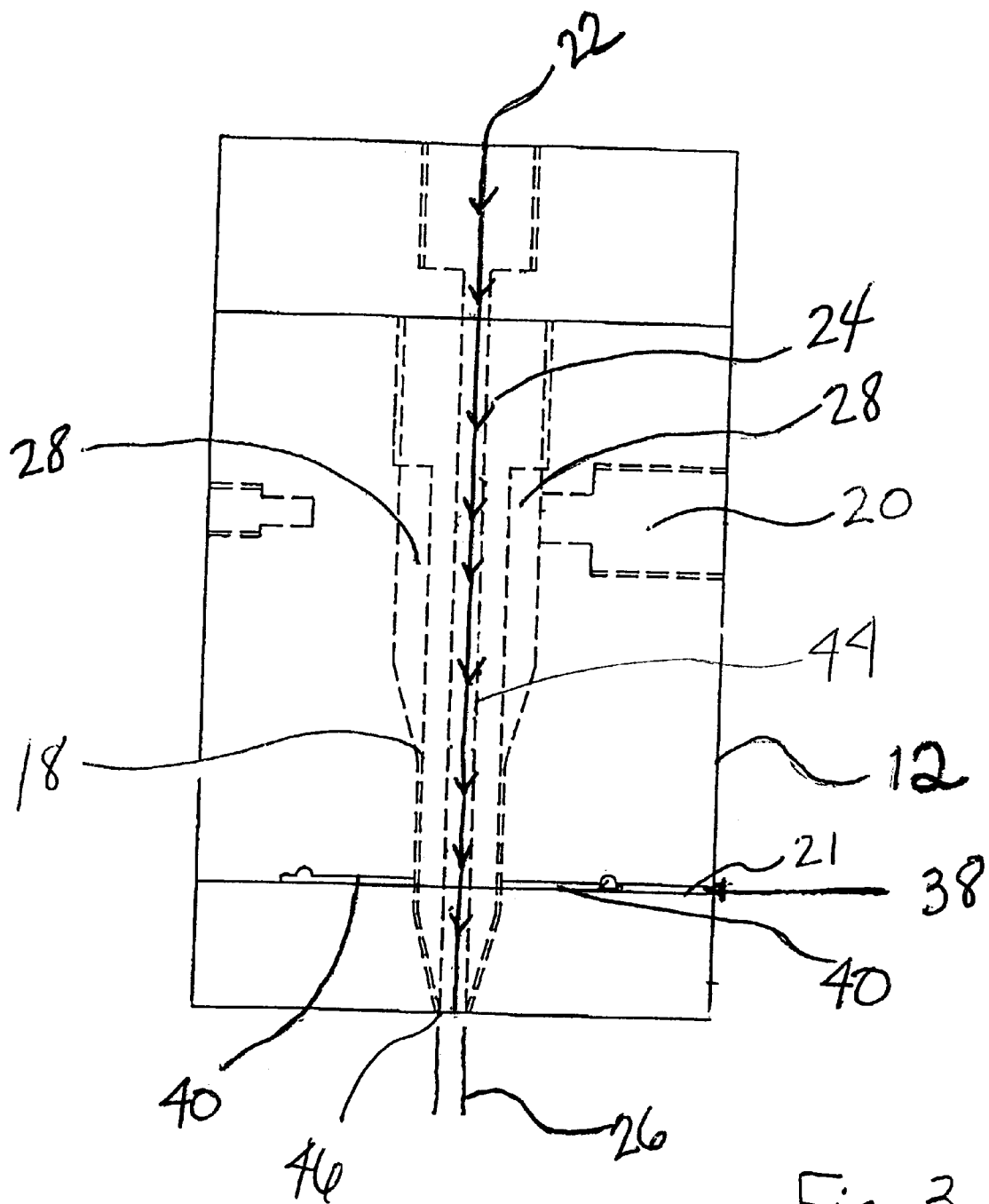
FIG. 3 shows generally as 12, an extrusion crosshead or extrusion shaping head unit designed for forming hollow tubular members which can be used in medical devices. The extrusion unit has a flow channel 38 through which the coating is pumped for coextrusion of the coating on the outer surface of the polymeric tubular member.

FIG. 3 shows generally at 12 an extrusion shaping head or crosshead unit for forming hollow polymeric tubing. This unit is similar in construction to those found in FIGS. 1 and 2 and has an entry port 20 for supplying a stream of molten polymeric material to a channel 28. Additionally, extrusion head 12 has a means 38 of supplying lubricious coating into a second entry port 21 which forces said coating into a half circle channel 40 in which coating material is circulated around, and thereby contacting the molten polymeric material. The means 38 of supplying the coating may be a volumetric gear pump, or other pumping means. The molten polymeric material is extruded through the extruder shaping mandrel 18 and is circulated around air flow channel 44 through which an air source 22 flows to maintain constant pressure and to facilitate a consistent tubing diameter. The tubing then exits the extruder shaping die through the discharge port 46 into a cool water bath with the coating on its outer surface.

One of skill in the art would recognize that various modifications may be made to the extrusion process without departing from the scope of the present invention.

The tubing 26 is formed from what is referred to herein as the polymeric base material, and may be comprised of any extrudable polymeric material from which medical devices are typically produced including various organic high polymers such as polyesters, polyamides, polyurethanes, polyurethaneureas, polyolefins such as polypropylene and polyethylene, polyolefin copolymers and terpolymers, polycarbonates, polyvinyl acetate, thermoplastic elastomers including polyether-polyester block copolymers such as the Hytrel® series of block copolymers, also referred to as thermoplastic polyester elastomers, available from DuPont in Wilmington, Del. or the Arnitel® series available from DSM, the Netherlands, such as Arnitel® 540 and polyamide/polyether/polyesters elastomers such as PEBAX® 6333, 7033 and 7233, polyvinyl chloride, polystyrene, polyacrylate, polymethacrylate, polyacrylonitrile, polyacrylamide, silicone resins, and so forth, and copolymers and blends thereof. This list is intended as an illustration of the types of materials which may be utilized in the present invention and is not intended as an exclusive list.

The tubular member may form any type of catheter including balloon catheters and stent delivery catheters, retractable sheaths or stent retaining sleeves for stent delivery catheters, guide wire lumens, pull wire lumens, and so forth.

Balloon catheters have an inflatable balloon, otherwise referred to as a dilatation balloon, mounted at the distal end. The tubular member of the present invention may be an extruded preform which is subsequently blown into a dilatation balloon. This is a typical method of balloon formation. The coating is applied to the preform prior to the preform exiting through the discharge port of the shaping die. The coating may provide lubricity to the balloon, as well as improve the durability of the balloon.

Suitable balloon forming techniques which may be employed are well known in the art and may be carried out in any conventional manner with conventional extrusion and blowing techniques. Such techniques for balloon formation are discussed in U.S. Pat. No. 4,490,421 to Levy and in U.S. Pat. No. 5,348,538 issued Sep. 20, 1994 to Wang et al. herein incorporated by reference.

Catheters assemblies are useful in a variety of medical procedures such as coronary angioplasty, stent delivery and placement for the opening of occluded or blocked blood vessels, for urological and reproductive surgeries, and to deliver biologically compatible fluids, such as radiologically opaque fluid for contrast x-rays to precise locations within the body.

The coating may comprise a liquid material. Preferably, the liquid material has good thermal stability, i.e. high degradation temperature, a high boiling point of greater than about 400° F. (204.4° C.), and a viscosity of about 300 cPs to about 1000 cPs at the temperature of application.

The coating preferably comprises a hydrophilic compound including alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylarnide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, and so forth. The polymers are typically chain-structured, non-crosslinked and water soluble having a hydrophilic group such as —OH, —CONH$_2$, —COOH, —NH$_2$, —COO—, —SO$_3$, —NR$_3^+$ and so forth where R is alkyl or hydrogen.

Derivatives of any of these polymers may be utilized providing that enough of the basic structure of the polymers above that provides water sensitivity, solubility or dispersibility is retained allowing the polymer to uptake enough water to swell or partially dissolve enough upon exposure to moisture to provide lubricity in such a way to reduce frictional forces between the surface it is coated on and another surface such as tissue, metal or polymeric surfaces. Water insoluble derivatives may be employed as long as they have the freedom in the molecular chain and can be hydrated. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above-mentioned water soluble polymers. Also useful are polymers crosslinked with substances having more than one reactive functional group such as diazonium, azide, isocyanate, acid chloride, acid anhydride, imino carbonate, amino, carboxyl, epoxy, hydroxyl, and aldehyde groups.

Further polymers include those copolymerized with vinyl, acrylic acid, methacrylic acid, diene compounds, and so forth.

Copolymers with vinyl groups, diene compounds and maleic anhydride may also be utilized.

The polyalkylene glycols or alkoxy polyalkylene glycols have the following general formula:

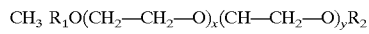

$CH_3$ $R_1O(CH_2—CH_2—O)_x(CH—CH_2—O)_yR_2$ $R_1$ and $R_2$ may be the same or different and can be H or an alkyl group having 1 to about 6 carbon atoms, x is from 2 to about 500; and y is from 0 to about 100.

The polyalkylene glycols and alkoxy polyalkylene glycols may also contain functional groups such as, for example, hydroxyl, sulfur, nitrogen or oxygen.

Hydrogel coatings may also be utilized which absorb water and swell upon exposure to an aqueous environment. Such polymers include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride and its derivatives; and so forth.

Carboxylic acid-containing polymers may form hydrogels such as copolymers of acrylic acid, methacrylic acid maleic acid, fumaric acid or other polymerizable ethylenically unsaturated acids. These compounds may optionally be neutralized.

Specific examples of hydrogel polymers include poly (ethylene-maleic anhydride) copolymers sold by Aldrich Chemical Co. and maleic anhydride-methyl vinyl ether copolymers sold by G.A.F. Corp. such as Gantrez® AN 169.

Maleic anhydride copolymers may also be chemically modified by partial reaction with a solution containing an anhydride or carboxylic acid reactive compound such as an amine, alcohol, epoxy or imine compound. The reactive compound may suitably be a low molecular weight monofunctional compound, in which case hydrophilicity will usually be reduced.

Another hydrogel polymer is one in which polyethylene oxide is captured in an interpenetrating crosslinked acrylic polymer network by polymerizing a mixture of an acrylic monomer composition comprising a monomer having plural (meth)acrylate groups and polyethylene oxide, thereby providing a hydrogel coating.

Monomeric materials may be useful for coating the polymeric tubes of the present invention. These monomeric materials can then be polymerized to create the coating layer. For instance, polymerization may be initiated through the use of actinic radiation including ultraviolet (UV) and election beam (EB) radiation. Other means of curing include chemical initiators, catalysts, heat, or any combination thereof. For instance, chemical initiators are commonly used in combination with UV radiation. Give some examples.

Polyfunctional compounds which produce surface crosslinking may also be employed. Polyethylene glycols or monohydroxy derivatives thereof may also be employed. Treatment of the coating with such reactive compounds may be combined with neutralization reactions of unreacted acid groups also obtained from the specific reactions or from hydrolysis of any unreacted anhydride groups remaining after such reactions.

The compounds of the present invention may be utilized in any combination to more narrowly tailor the resultant composition to the application. For instance, some of the hydrophilic polymers of the present invention exhibit less flexibility than others such as the hydrogels found in the previous paragraph. The flexibility may be improved by the addition of polyethylene oxide/polypropylene oxide copolymers, especially block copolymers, polyvinyl pyrrolidone, polyvinyl alcohol, and so forth.

In general hydrophilic coating materials are preferred as coating materials for use in the invention. They are more biocompatible and less irritating to human tissue than are hydrophobic coatings. The hydrophilic compounds can provide both lubricity and increased wearability to a balloon structure.

Examples of some of the preferable hydrophilic coating materials include the homopolymers and copolymers of vinyl pyrrolidone; polyacrylamides; polyethylene oxides; polyvinyl alcohols; (meth) acrylic acid homopolymers and copolymers; ionomeric polymers; polycarboxylic acids (optionally mixed with polyurethane); and so forth.

Polymers may be applied to the tubular member in a molten state. For ease of application, these materials will preferably have a viscosity of about 100 to about 1000 at the temperature of application. The coating thickness may be adjusted by changing the viscosity of the molten polymer and the feeding rate of the gear pump that supplies the molten polymer.

The coating thickness is about 1 to about 20 $\mu$m, preferably from about 1 to about 10 $\mu$m, more preferably from about 2 to about 6 $\mu$m and most preferably from about 2 to about 4 $\mu$m.

Utilizing the method of the present invention, the coating and the polymeric tube come into contact at elevated temperatures, i.e. at a temperature greater than ambient so as to improve the retention of the coating on the tube. The polymeric tubing may be at temperatures as high as 200° C. when the coating is applied as the coating is applied prior to the tubing exiting the extruder. Preferably, the temperature at the interface of the polymeric tubing and the coating will be greater than about 100° C., more preferably greater than about 120° C., and even more preferably greater than about 150° C. The higher the temperature, the more flowable the polymers will be, and subsequently, the mixing between the two should also be better, resulting in better adhesion. However, the temperature cannot be so high as to avoid melting or degrading the polymeric tube.

The coating may be applied at ambient temperatures, but the coating may be applied at elevated temperatures of about 100° C. to about 300° C. as well. For instance, the polymers may be applied out of the melt, i.e. when they are in a molten state. For most polymers, temperatures of application may vary between about 120° C. and about 205° C., and preferably between about 135° C. and about 190° C.

The higher the molecular weight of the polymer, the higher the application temperature required to render the material flowable enough to apply. The type of application will also play a role in determining how the coating may be applied. Some types of application methods require lower viscosities than others.

It is desirable to the present invention to achieve interpenetration at the interface between the low friction or coating, and the polymeric tube. It is surmised that the better the interpenetration between the two polymeric materials at the interface, the better the coating will be retained on the surface, and the more permanent the coating on the medical device. It is further surmised that better interpenetration can be achieved if the temperature at which the polymeric materials come into contact is elevated.

Essentially, the polymers, both the coating and polymer from which the tube is formed, must be at a temperature high enough so that they may flow and intermingle, thus resulting in interpenetration of the polymers occurring at the interface. It is surmised that molecules that are not located at the interface, are not interpenetrating.

The coating method of the present invention may be utilized to apply coatings on tubular members used in medical devices. The coatings may add lubricity to the device, as well as improving the durability of the device including improving the resistance to scratches, abrasions and punctures. This is particularly important for dilatation balloons.

The coatings of the present invention can be utilized to lower the coefficient of friction between the various parts of a catheter assembly which come into a moving or sliding relationship with one another. A common problem which occurs in catheter assemblies is friction or adhesion between various parts which occasionally come into contact with one another during the medical procedure. For instance, friction can occur between the guide catheter and guide wire, between the introducer sheath and the guide catheter, or between the guide catheter and the balloon catheter, for instance, and may increase the difficulty of insertion, cause loss of catheter placement, and result in discomfort to the patient or damage to the vasculature. It is therefore desirable to reduce the friction due to the sliding between the various parts of the catheter assemblies. For instance, guide catheters are introduced over a guide wire through a previously placed introducer sheath and advanced through a blood vessel to a precise location, such as a location of a stenosis. It is important that friction between the various parts of the catheter device is minimized.

The coatings of the present invention may therefore be utilized to improve the deployment of any of stents, stent-grafts, grafts or vena cava filters, or other such expandable medical devices, by coating the inner surface of the polymeric sheath to reduce the friction between the sheath and the stent.

The coatings of the present invention can also be used to improve the durability of, as well as add lubricity to, dilatation balloons, especially those formed of non-compliant balloon materials. The balloon wall may be noncompliant or compliant. Noncompliant balloons are formed from relatively stiff materials including polyethyleneterephthalate (PET), high density polyethylene, polyarnides, polycarbonates and stiff polyurethanes, and so forth. The balloon wall may also be compliant and made of materials such as polyvinyl chloride, polyethylene, polyester copolymers, polyolefin copolymers and so forth. The present invention provides a particular advantage when the balloon wall is made of a stiff, noncompliant material. Such materials tend to scratch more easily, especially if a fold occurs in the balloon. Scratches, abrasions and punctures on these balloons can ultimately result in damage to blood vessels.

There are vast number of various types of catheter devices commercially available and the present inventors envision that the coating method described herein may be employed in any such device.

The devices discussed herein are meant only for illustration as to how the coatings of the present invention may be utilized, and are in no way intended to limit the present invention. One of skill in the art would understand how to incorporate the coatings and method of the present invention to any other such devices.

What is claimed is:

1. A method of preparing a flexible polymeric catheter tube having an inner surface and an outer surface useful in medical devices using a single extruder and comprising forcing a stream of a molten base polymer into an entry port at one end of the extruder shaping die said shaping die also having a discharge port, and applying a hydrophilic lubricious coating to said tube at a coating thickness that is about 0.2% to about 20% of the total of the wall thickness of the tube and the thickness of the coating prior to said tube exiting said discharge port.

2. The method of claim 1 wherein said coating is sprayed on said inner surface of said tube immediately prior to said tube exiting said discharge port.

3. The method of claim 1 wherein said coating is applied to said inner surface of said tube by pumping said coating to a channel in said extruder unit.

4. The method of claim 1 wherein said coating is applied to said outside surface of said tube by pumping said lubricious coating to a circular channel wherein said lubricious coating is circulated around said tube at a point prior to exiting said extruder unit.

5. The method of claim 1 wherein said tube is a preform for a dilatation balloon.

6. The method of claim 5 wherein said balloon is formed from a non-compliant thermoplastic polymer.

7. The method of claim 5 wherein said balloon is formed from a thermoplastic polymer selected from the group consisting of polyethelene terephthalate, high density polyethelene, polyamides, polyether block amides, polycarbonates and stiff polyurethanes, and mixtures thereof.

8. The method of claim 1 wherein said tube is utilized in a catheter assembly.

9. The method of claim 1 wherein said tube is comprised of at least one member selected from the group consisting of polyesters, polyamides, polyurethanes, polyurethaneureas, polyolefins, polycarbonates, polyvinyl acetate, thermoplastic elastomers, polyvinyl chloride, polystyrene, polyacrylate, polymethacrylate, polyacrylonitrile, polyacrylamide, silicone resins, copolymers and terpolymers thereof, and mixtures thereof.

10. The method of claim 1 wherein said coating is a liquid at room temperature.

11. The method of claim 1 wherein said coating is a solid at room temperature.

12. The method of claim 1 wherein said hydrophilic lubricious coating comprises at least one compound selected from the group consisting of polyalkylene glycols, alkoxy polyalkylene glycols, phosphazenes, poly(2-ethyl-2-oxazoline), copolymers of methylvinyl ether and maleic acid, poly(vinylpyrrolidone), polyvinylsulfonic acid, poly(N-alkylacrylamide), poly(acrylic acid), poly(vinyl alcohol), polyalkylene oxide-modified polydimethylsiloxanes, poly(ethyleneimine), polyamides, methyl cellulose, carboxymethylcellulose, heparin, dextran, modified dextran, hydroxyalkylated chitin, hyaluronan, and mixtures thereof.

13. The method of claim 1 wherein said hydrophilic lubricious coating comprises a monomer.

14. The method of claim 13 wherein said monomer is polymerized on said surface of said tube.

15. The method of claim 14 wherein said polymerization is initialized by a method selected from the group consisting of chemical, thermal, ultraviolet, electron beam, and mixtures thereof.

16. The method of claim 1 wherein said coating thickness is about 1 to about 10 $\mu$m.

17. The method of claim 1 wherein said hydrophilic lubricious coating has a viscosity of about 100 cPs to about 1000 cPs at the temperature of application.

18. The method of claim 16 wherein said coating is applied to said tube in a molten state.

19. The method of claim 1 wherein said coating lowers the coefficient of friction between said tube and a secondary surface.

20. A method of preparing a flexible polymeric catheter tube having an inner surface and an outer surface useful in medical devices using a single extruder comprising forcing a stream of molten base polymer into an entry port at one end of the extruder shaping die said shaping die also having a discharge port, and applying a lubricious coating by spraying said lubricious coating on said tube or by pumping said lubricious coating to a channel in said extruder shaping head and circulating said lubricious coating around said tube thereby applying said coating to said tube prior to said tube exiting said discharge port.

21. The method of claim 20 wherein said lubricious coating has a viscosity from about 100 cPs to about 1000 cPs.

22. The method of claim 20 wherein said lubricious coating is a liquid at room temperature.

23. The method of claim 1 wherein said coating thickness is about 1 micron to about 10 microns.

* * * * *